United States Patent [19]

Barberet et al.

[11] Patent Number: Plant 6,370

[45] Date of Patent: Nov. 1, 1988

[54] CARNATION NAMED 'LONSTIGA'

[75] Inventors: Nicole Barberet; Yves Ducloux, both of Antibes, France

[73] Assignee: Laboratoire de Physiologie Vegetale de la Londe, La Londe, France

[21] Appl. No.: 907,861

[22] Filed: Sep. 15, 1986

[51] Int. Cl.[4] ..... A01H 5/00

[52] U.S. Cl. ..... Plt./73

[58] Field of Search ..... Plt./70, 73

*Primary Examiner*—Robert E. Bagwill

*Attorney, Agent, or Firm*—Charles W. Rummler

[57] ABSTRACT

A new variety of spray carnation having small, bright red blooms provided profusely at intermittent intervals of spring, midseason and fall appearing in clusters at the upper portion of a strong, erect stem, the flowers being distinguished by the strong cardinal red color of the petals which are lightly striated with longitudinally-extending white lines and the plant itself being distinguished by its very tall growth and vigorous, upright and rather rigid habit with moderately abundant foliage.

1 Drawing Sheet

BACKGROUND OF THE NEW PLANT

This new carnation variety originated as a seedling resulting from our crossing of plants selected from our collection of carnations maintained for breeding purposes at La Londe, Les Maures, France, our object in making this crossing being to develop a spray carnation having blooms of good quality and nice color on a strong plant having resistance to *Fusarium oxysporum.* This plant was reproduced by cuttings with very good results so that further propagation was directed to be carried on through a series of successive generations by means of cuttings from previous plants produced in the same manner. This extended propagation of our new seedling demonstrated clearly that the novel characteristics of its blooming and growth habits would remain true from generation to generation and appeared to be firmly fixed.

DESCRIPTION OF THE DRAWING

Our new variety of spray carnation is illustrated by the accompanying photographic drawing, which shows in full color the upper portion of a typical spray stem bearing buds and flowers at various stages of growth, the colors shown being as nearly true to those specified as is reasonably possible to obtain by conventional photographic procedures.

DESCRIPTION OF THE NEW PLANT

The following is a detailed description of our new carnation plant based upon observations of greenhouse plants grown at La Londe, Les Maures, France, the color designations being according to The R.H.S. Colour Chart published by The Royal Horticultural Society of London, England.

THE PLANT

Origin: Seedling.

Parentage:

*Seed parent.*—Stock Variety 75 MR 16.

*Pollen parent.*—Stock Variety 79 MFG 2. These parent varieties were selected by us from our collection of breeding plants and each is individually identified in our permanent records maintained in our office at La Londe.

Classification:

*Botanic.*—*Dianthus caryophyllus* hybrid.

*Commercial.*—Spray Carnation.

Form: Bush of tall spray shape comprising at least four stems emitted from the main stem near the ground.

Main stem:

*Length.*—Less than about 15 cm. due to pinching.

Branching character: Alternate and numerous.

Growth: Vigorous, upright and rather rigid.

Foliage:

*Quantity.*—Moderately abundant.

*Number of leaves.*—More than 120.

*Size of leaf.*—Leaf averages about 11.6 cm. long and about 1 cm. wide at the seventh node.

*Leaf shape.*—Lanceolate with rolled margins.

*Texture.*—Leathery.

*Color.*—Both upper and lower sides, 189A/B.

*Leaflets.*—None.

*Ribs, veins and rachis.*—Hardly noticeable.

THE BUD

Size: Small.

*Diameter.*—Averages about 1.3 cm.

*Length.*—Averages about 2.5 cm.

Shape: Ovoid.

Rate of opening: Normal for carnations.

Color of petals:

*When sepals first divide.*—185A/B.

*When petals begin to unfurl.*—Cardinal Red, 53A, and lightly striated with white.

Sepals:

*Number.*—5 to 6.

*Shape.*—Joined together at lower part with the upper part somewhat oval in shape and having a sharp pointed apex. The sepals are hooded over the bud before dividing and continue to stand up as the flower opens.

*Color.*—Inside — 145D and lightly 185C. Outside — 143C, 144C and lightly 185C.

*Striae.*—Longitudinal.

Calyx: Small and of cylindrical shape.

*Aspect.*—Smooth; the calyx does not split.

Flower stem:

*Length.*—About 69 cm., in average.

*Character.*—Erect and rather rigid.

*Color.*—189A/B.

THE FLOWER

Blooming habit: Recurrent, blooming profusely during spring, midseason and fall blooming periods with a tendency to give fewer blooms in the fall.

Size of bloom: Small.

*Diameter.*—Averaging about 5 cm.

*Depth.*—Averaging about 2.8 cm.

Borne: As a cluster.

Shape:

*When bloom first opens.*—High centered.

*When bloom matures.*—Dome shaped.

Petalage:

*Number of petals.*—About 42 to 54.

*Arrangement.*—Imbricated.

*Petal form.*—Fan shaped with rounded edges and lightly serrated apex.

*Texture.*—Leathery.

*Appearance.*—Velvety.

*Color.*—Both outer and inner petals: Body — 53A, lightly striated with white. Base — Greenish. Reverse side — 185A/B.

Petaloids: Less than 10.

*Size.*—Smaller than petals.

*Color.*—Same as petals.

Flower stem:

*Length.*—Averaging about 69 cm. (cut at the tenth node).

*Character.*—Strong and upright.

*Color.*—189A/B.

Discoloration after full bloom: Weak.

Fragrance: Strong.

Persistence: The flowers hang on and dry.

Lasting quality:

*As a cut flower.*—At least 10 days in vase keeping.

REPRODUCTIVE ORGANS

Stamens:

*Number.*—7 to 15.

*Arrangement.*—Around the ovary.

*Anthers.*—Size: Less than 4 mm. Color: Garnet.

*Filaments.*—Length: Averages about 2.3 cm. Color: White.

*Pollen.*—Color — Garnet.

Pistils:

*Number.*—2 to 4.

*Styles.*—Length: Averaging about 2.3 cm. Color: Garnet.

*Stigmas.*—Color: Garnet.

Ovaries: The ovaries are ribbed.

This new spray carnation variety most nearly resembles the variety 'Londrina' (U.S. Plant Pat. No. 3,570) but differs from that variety by being very resistant to *Fusarium oxysporum.*

We claim:

1. The new and distinct variety of spray carnation, substantially as herein shown and described, characterized by its intermittent flowering habit with profuse production of flowers having a substantially solid cardinal red coloration, and having a rapid, vigorous and upright growth habit with a normal height of about 123 cm. at eight months with flower stems averaging about 69 cm. in length.

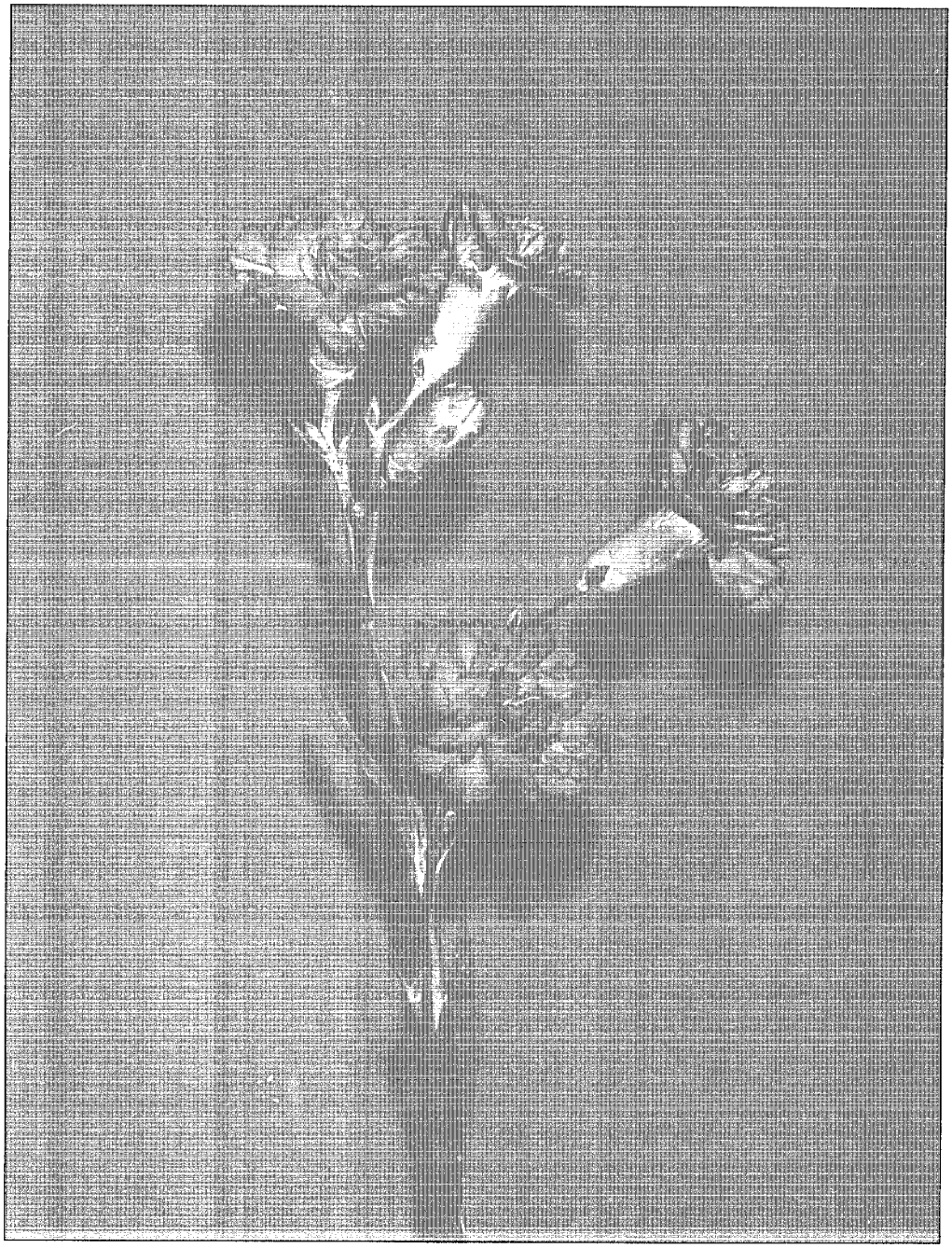

* * * * *